United States Patent [19]

Summers, III et al.

[11] Patent Number: 4,751,318

[45] Date of Patent: Jun. 14, 1988

[54] METHOD OF MAKING ORGANIC SOLVENT SOLUBLE ZINC ALKOXY ALKOXIDES

[75] Inventors: William Summers, III, Peekskill; Eric W. Burkhardt, Brewster, both of N.Y.

[73] Assignee: Stauffer Chemical Company, Westport, Conn.

[21] Appl. No.: 861,391

[22] Filed: May 9, 1986

[51] Int. Cl.⁴ .............................................. C07F 3/06
[52] U.S. Cl. .................................................... 556/130
[58] Field of Search ........................................ 556/130

[56] References Cited

U.S. PATENT DOCUMENTS

| | | | |
|---|---|---|---|
| 2,229,528 | 1/1941 | Shoemaker | 556/130 X |
| 3,255,257 | 6/1966 | Brindell et al. | 556/130 X |
| 3,304,288 | 2/1967 | King | 556/130 X |
| 4,544,761 | 10/1985 | Taylor et al. | 556/130 |

OTHER PUBLICATIONS

J. Chem. Soc. (B), pp. 1020–1024 (1966); Chemical Abstracts 65 20159d (1966).

*Primary Examiner*—Helen M. S. Sneed

[57] ABSTRACT

Organic solvent soluble zinc alkoxides are prepared by the reaction of dialkyl zinc with an alkoxy alcohol.

8 Claims, No Drawings

METHOD OF MAKING ORGANIC SOLVENT SOLUBLE ZINC ALKOXY ALKOXIDES

BACKGROUND OF THE INVENTION

Alkoxides of divalent metals are generally capable of preparation by the reaction of an elemental metal with an alcohol. The preparation of zinc alkoxides by the foregoing method has generally been unsuccessful. Moreover, many simple alkoxides of zinc have little or no solubility in organic solvents.

The difficulty of preparation and the relative insolubility of simple zinc alkoxides is disadvantageous for processes where it is desirable to form solutions having intimately mixed metal alkoxide solutes.

U.S. Pat. No. 3,717,666 describes reaction products of aluminum reacted with alkoxy alcohols that have utility as catalysts. Alloys of aluminum with a list of metals including zinc are proposed as reactants for catalyst alkoxide formation (Col. 5, line 36).

It is desirable to provide new methods of preparing organic solvent soluble alkoxides of zinc.

FIELD OF THE INVENTION

This invention relates to the formation of novel zinc alkoxides, methods of making such alkoxides, and processes of using said alkoxides.

DETAILED DESCRIPTION OF THE INVENTION

Metal alkoxides (also called metal alcoholates) are compounds having a metal attached to alkyl groups by an oxygen atom. Many alkoxides of polyvalent metals are industrially important, for example, the organic solvent soluble alkoxides of "metals" such as zinc, aluminum, silicon, titanium, vanadium, and zirconium.

COMPOUNDS OF THE INVENTION

It is a discovery of this invention that zinc alkoxy alkoxides are generally organic solvent soluble. The defining characteristic of an alkoxide being "organic solvent soluble" is defined herein to be a solubility of at least 15 weight percent at ambient (approx. 20° C.) temperature in toluene or 2-methoxy ethanol or 2-butoxy butanol.

The alkoxides of this invention are novel compounds represented by the following formula:

$$(R_1O-(CH_2)_n-O)-Zn-(O-(CH_2)_m-OR_2)$$

where m and n are the same or different positive integers from 1 to 12; and $R_1$ and $R_2$ are the same or different hydrocarbyl radicals of from 1 to 20 carbon atoms. Preferably n and m are integers from 1 to 4 and $R_1$ and $R_2$ are alkyl radicals of from 1 to 12 carbon atoms.

The metal alkoxy alkoxides of this invention are often prepared in such a manner that the alkoxy alkoxide moieties are the same and may be represented by the formula:

$$Zn(O-(CH_2)_n-OR_1)_2$$

where n and $R_1$ are as previously defined.

Mixtures containing any combination of the zinc alkoxy alkoxides described in the preceding two paragraphs are also within the scope of this invention.

Particularly preferred $R_1$ or $R_2$ groups are those with one to four carbon atoms, such as methyl, ethyl, propyl, and butyl. Examples of specific alkoxides of this invention are as follows:

zinc bis (2-methoxyethylate)
zinc bis (2-ethoxyethylate)
zinc bis (2-butoxyethylate)
zinc bis (3-methoxypropylate)
zinc bis (3-ethoxypropylate)
zinc bis (3-propoxypropylate)
zinc bis (3-methoxybutylate)
or mixtures of the above compounds.

The zinc alkoxy alkoxides are organic solvent soluble liquids or solids. These compounds are generally reactive with atmospheric oxygen and moisture and should be stored in a protected environment.

METHOD OF MAKING ZINC ALKOXY ALKOXIDES

The alkoxides of zinc are synthesized according to the process of this invention by reacting a dialkyl zinc reactant with an alkoxy alcohol containing alcohol reactant.

The dialkyl zinc compound reactant is represented by the formula:

$$R_2-Zn-R_3$$

wherein $R_2$ and $R_3$ are the same or different and are selected from alkyl groups having from 1 to 20 carbon atoms. Preferably the alkyl groups have from 1 to 4 carbon atoms. Typical zinc compounds having utility in the process of the invention are dimethyl zinc, diethyl zinc, and dibutyl zinc.

The alkoxy alcohol containing alcohol reactant may be entirely composed of alkoxy alcohol or may be a mixture of alkoxy alcohols with simple alcohols. Simple alcohols are alcohols reactive with Group IIA or Group IIIA metals, said simple alcohols being represented by the formula:

$$R_1-OH$$

wherein $R_1$ is a hydrocarbyl group of from 1 to 20 carbon atoms. Preferably $R_1$ is an alkyl group of from 1 to 4 carbon atoms. Useful $R_1$ groups include ethyl, propyl and butyl.

The alkoxy alcohol component of the alcohol reactant is represented by the formula:

$$HO-(CH_2)_m-OR_1$$

wherein m is a positive integer from 1 to 12 and $R_1$ is a hydrocarbyl group having 1 to 20 carbon atoms. Preferably, m has a value from 1 to 4 and $R_1$ is an alkyl group of from 1 to 12 carbon atoms. Useful alkoxy alcohols include the following:

2-methoxy ethanol
2-ethoxy ethanol
3-methoxy propanol
3-ethoxy propanol
3-propoxy propanol
3-butoxy propanol
3-methoxy butanol The molar proportions of (1) dialkyl zinc reactant and (2) alkoxy alcohol containing alcohol reactant are not critical. Approximately stoichiometric proportions of the reactants may be used, for example, two moles of alkoxy alcohol reacted with one mole of dialkyl zinc. It is usually preferred to have an excess of alcohol to remove the dialkyl zinc reactant from the reaction medium and make subsequent processing of the alkoxide product easier. The alcohol is present in the reaction medium most preferably in a molar proportion equivalent to at least 110 percent of the stoichiometric requirements of the metal.

It is an essential aspect of this invention to have an amount of alkoxy alcohol in the alcohol reactant that on the average replaces at least one bond of the zinc in the dialkyl zinc reactant with an alkoxy alcohol moiety. The balance of the alkoxy alcohol containing alcohol reactant may be a simple alcohol reactive with the dialkyl zinc. Preferably, at least one-half of the moles of alcohol in the alcohol containing reactant are alkoxy alcohol.

The reaction medium may be a mixture of an inert solvent and liquid alcohol. For example, a mixture of toluene and 2-methoxy ethanol may be employed.

The temperature of reaction is not critical and typically ranges from the ambient temperatures up to the boiling point of the reaction medium.

Typically, the formation of the zinc alkoxy alkoxides is substantially completed in ½ to 12 hours.

Purification of the reaction product is often not necessary in instances where the product is in a useful solution form capable of being mixed and coprocessed with other materials. However, if desired, the alkoxy alkoxides may be separated from their reaction medium by a variety of techniques such as solvent stripping, solvent extraction and recrystallization.

One or more zinc alkoxy alkoxides of the invention may be formed in the same reaction. For example, a mixture of zinc dialkyls may be placed in a reaction medium with one or more suitable alcohols. Moreover, the zinc dialkyl may be mixed with metals known to form soluble alkoxides. For example, the elements aluminum, titanium, silicon, vanadium, and zirconium or mixtures thereof may be simultaneously reacted with alkoxy alcohols together with zinc dialkyls to give mixtures of soluble alkoxy alkoxides.

The alcohol reactant may itself consistute the reaction medium. Alternatively, an unreactive aromatic, aliphatic, or cycloaliphatic diluent such as cyclohexane, toluene, octane, or mixtures thereof may be used as all or part of the reaction medium.

HOMOGENEOUS LIQUID COMPOSITIONS OF THE INVENTION

Useful compositions comprise as essential ingredients: (1) one or more zinc alkoxy alkoxides, and (2) an organic solvent.

The ingredient (1) dialkyl zinc has been previously defined.

The ingredient (2) organic solvent is a alkoxide non-reactive liquid that is capable of dissolving at least 15 percent by weight of alkoxide ingredients (1).

Useful solvents include the following:
2-methoxy ethanol
2-ethoxy ethanol
2-methoxy propanol
2-ethoxy propanol
2-propoxy propanol
2-butoxy propanol
cyclohexane
toluene
heptane
octane An optional ingredient (3) comprises an organic solvent soluble alkoxide capable of hydrolysis. Ingredient (3) alkoxides may comprise alkoxides of Group IIA metals, Group IIIA metals, aluminum, titanium, silicon, vanadium, zirconium or mixtures thereof.

Solutions of zinc alkoxy alkoxides are formed by contacting with agitation the solvent and alkoxide.

A general procedure for utilizing liquid compositions containing zinc alkoxides is to hydrolyze the alkoxide to form a precipitate, then dry the precipitate to form a high purity metal oxide product. Details of this procedure are given in Columns 3 and 4 of U.S. Pat. No. 3,946,102; the disclosure of which is incorporated herein by reference.

The method and composition of the invention are illustrated in the following examples:

EXAMPLE 1A

This example illustrates the synthesis of $Zn(OCH_2CH_2OCH_3)_2$.

Diethylzinc (100 ml of a 15 wt. % solution in toluene) was slowly added to 2-methoxyethanol (50 ml) with the rapid release of ethane. The resulting colorless solution had no insoluble material after storage for more than three weeks, indicating the enhanced solubility of this alkoxide over normal zinc alkylates. The compound is soluble in toluene (5%) and methoxyethanol (25%) and is insoluble in aliphatic hydrocarbons.

EXAMPLE 1B

This example illustrates the synthesis of $Zn(OCH_2CH_2OCH_2CH_3)_2$. The general procedure of Example 1A is followed except 97 ml of ethoxyethanol is used. Evaporation of solvent gave a yellow, semi-crystalline solid in 89% yield. The compound is soluble in toluene (10%) and ethoxyethanol (25%) and is insoluble in aliphatic hydrocarbons.

We claim:

1. Alkoxy alkoxides represented by the formula:

$$(Z-(CH_2)_n-O)-Zn-(O-(CH_2)_m-OR_2)$$

wherein n and m are the same or different and are each selected from positive integers from 1 to 12; Z is $(R_1O)-$ or $(R_1)-$ and $R_1$ and $R_2$ are the same or different hydrocarbyl radicals of from 1 to 20 carbon atoms with the proviso that m and n are not both 2, $R_2$ is not methyl, and Z is not $(R_1O)-$ with $R_1$ also methyl.

2. The alkoxy alkoxides of claim 1 wherein n and m are integers from 1 to 4 and $R_1$ and $R_2$ are alkyl radicals containing 1 to 12 carbon atoms.

3. Alkoxy alkoxides of claim 1 selected from zinc bis (ethoxyethylate), zinc bis (methoxypropylate), zinc bis (ethoxypropylate), or zinc bis (butoxypropylate).

4. A method of making an organic solvent soluble zinc alkoxy alkoxide by reacting (1) a dialkyl zinc compound represented by the formula:

$$R_1-Zn-R_2$$

wherein $R_1$ and $R_2$ are the same or different and are selected from hydrocarbyl groups of from 1 to 20 carbon atoms, and (2) an alkoxy alcohol represented by the formula:

$$R_1O-(CH_2)_n-OH$$

wherein $R_1$ is a hydrocarbon radical of from 1 to 20 carbon atoms and n is a positive integer from 1 to 12 with the proviso that n is not 2 and $R_1$ is also not methyl.

5. The method of claim 4 wherein the alkoxy alcohol is selected from the group methoxyethanol, ethoxyethanol, propoxyethanol, butoxyethanol, methoxypropanol, ethoxypropanol, propoxypropanol, butoxypropanol.

6. A method of making organic solvent soluble alkoxides of zinc by reacting:
(a) a dialkyl zinc compound represented by the formula:

$$R_2-Zn-R_3$$

wherein $R_2$ and $R_3$ are the same or different and are selected from alkyl groups of from 1 to 20 carbon atoms, and;
(b) an alkoxy alcohol containing alcohol reactant comprising:
(i) one or more alkoxy alcohols represented by the formula:

$$R_1O-(CH_2)_m-OH$$

and;
(ii) one or more simple alcohols represented by the formula:

$$R_1-OH$$

wherein for (i) and (ii), $R_1$ is a hydrocarbyl group of from 1 to 20 carbon atoms, and m is a positive integer from 1 to 12; with the proviso that the alkoxy alcohol content of the alcohol reactant be sufficient to satisfy on the average at least one-half of the stoichiometric alcohol requirements of the dialkyl zinc reactant.

7. The process of claim 6 wherein substantially all of the alcohol reactant comprises the alkoxy alcohol.

8. The process of claim 6 wherein $R_1$ is an alkyl group having 1 to 12 carbon atoms and m has a value from 1 to 4.

* * * * *